United States Patent [19]

Frank et al.

[11] 4,196,149

[45] Apr. 1, 1980

[54] TERNARY SALTS OF TRIS(AMINOMETHYL)PHOSPHINES AND THEIR OXIDES

[75] Inventors: Arlen W. Frank, Slidell; Donald J. Daigle, New Orleans; Russell M. H. Kullman, Harahan, all of La.

[73] Assignee: The United States of America as represented by the Secretary of Agriculture, Washington, D.C.

[21] Appl. No.: 964,854

[22] Filed: Nov. 29, 1978

[51] Int. Cl.² ............................................. C07C 83/00
[52] U.S. Cl. .................................................. 260/583 E
[58] Field of Search ......................... 260/583 E, 583 R

[56] References Cited

U.S. PATENT DOCUMENTS

| | | | |
|---|---|---|---|
| 2,200,543 | 5/1940 | Dickey et al. | 260/606.5 P X |
| 3,035,053 | 5/1962 | Coates et al. | 260/583 E X |
| 3,037,978 | 6/1962 | Coates et al. | 260/583 E X |
| 3,253,033 | 5/1966 | Maier | 260/606.5 P |
| 3,442,948 | 5/1969 | Wiley | 260/606.5 P X |
| 3,496,231 | 2/1970 | Maier | 260/606.5 P X |
| 3,732,316 | 5/1973 | Lin | 260/606.5 P |
| 3,987,098 | 10/1976 | Frank et al. | 260/568 |

FOREIGN PATENT DOCUMENTS

| | | | |
|---|---|---|---|
| 842593 | 7/1960 | United Kingdom | 260/583 E |
| 854182 | 11/1960 | United Kingdom | 260/583 E |

OTHER PUBLICATIONS

Daigle et al., J. Heterocyclic Chem., 11 407 (1974).
Trostyanskaya et al., Zh. Obshch. Khim 37 1655–1657 (1967).
Mironova et al., Zh. Obshch. Khim. 42 2152–2158 (1972).
Daigle et al., Text Research J. 40 580–581 (1970).
Chemical Abstracts 68, 13084j(1968).

*Primary Examiner*—Helen M. S. Sneed
*Attorney, Agent, or Firm*—M. Howard Silverstein; David G. McConnell; Raymond C. VonBodungen

[57] ABSTRACT

Novel ternary salts of tris(aminomethyl)phosphines and their oxides having the formula $(R_2NH^+CH_2)_3P(O)_n3X^-$, wherein R is hydrogen, an alkyl radical having from 1 to 6 carbon atoms or an aryl radical, n is an integer from 0 to 1, and X is a halogen, are prepared by the reaction of a hydrohalic acid, HX, with various nitrogen- and phosphorus-containing compounds including tris(aminomethyl)phosphines and their oxides, tris(N-carbalkoxylaminomethyl)phosphines oxides, and 1,3,5-triaza-7-phposphaadamantane and its 7-oxide.

5 Claims, No Drawings

TERNARY SALTS OF TRIS(AMINOMETHYL)PHOSPHINES AND THEIR OXIDES

CROSS-REFERENCES TO RELATED APPLICATION

Ser. No. 964852, Filed 11-29-78 TRIS (N-CARBALKOXYLAMINOMETHYL)PHOSPHINE OXIDES AND SULFIDES.

BACKGROUND OF THE INVENTION (1) Field of the Invention

This invention relates to novel ternary salts of tris-(aminomethyl)phosphines and their oxides, and to methods for preparing the same.

(2) Description of the Prior Art

The unsubstituted tris(aminomethyl)phosphine, $(NH_2CH_2)_3P$, is unknown. The corresponding oxide, $(NH_2CH_2)_3PO$, is accessible only through the Gabriel synthesis from tris(chloromethyl)-phosphine oxide, $(ClCH_2)_3PO$ [Trostyanskaya, et al., Zh. Obshch. Khim., 37, 1655-57 (1967)]. It formed a crystalline salt, m.p. above 320° C., with hydrochloric acid, identified as the monohydrochloride salt by elemental analysis and molecular weight determination. Significantly, no ternary salt was reported. The fully substituted reagents, $(R_2NCH_2)_3P(O)_n$ (R=alkyl or aryl, n=0 or 1) are accessible by the reaction of dialkylamines with tetrakis(hydroxymethyl)phosphonium chloride (THPC) [Coates and Hoye, U.S. Pat. No. 3,035,053 (1962)], tris-(acetoxymethyl)phosphine [Mironova et al., Zh. Obshch. Khim., 42, 2152-58 (1972)], or white phosphorus and formaldehyde [Maier, U.S. Pat. No. 3,359,266 (1967)], or by the reaction of diarylamines with neutralized THPC [Daigle et al., Text. Research J., 40, 580-81 (1970)]. The partially substituted reagents, $(RHNCH_2)_3P(O)_n$ (R=aryl, n=0 or 1) are accessible by the reaction of arylamines with THPC [Frank and Drake, Jr., U.S. Pat. No. 3,987,098 (1976)] and other methods described therein; those reagents in which R=alkyl, n=0 or 1 are, to the best of our knowledge, unknown.

SUMMARY AND OBJECTS OF THE INVENTION

This invention relates to new and novel compounds of tris(aminomethyl)phosphine and its oxide having the general formula $(R_2NH^+CH_2)_3P(O)_n 3X^-$ wherein R is hydrogen, an aklyl radical having from 1 to 6 carbon atoms, or an aryl radical, n is an integer from 0 to 1, and X is a halogen.

Further, it includes processes for preparing a ternary salt of tris(aminomethyl)phosphine oxide which comprises hydrolyzing a tris(N-carbalkoxylaminomethyl)-phosphine oxide having the formula $(R'O_2CNHCH_2)_3PO$, wherein R' is an alkyl radical having from 1 to 6 carbon atoms, with six or more parts of a hydrohalic acid HX, where X is a halogen, until all three of the acyl-nitrogen bonds are cleaved, and recovering the product therefrom.

It further includes process of preparing ternary salts of tris(aminomethyl)phosphine and its oxide which comprises hydrolzying a 1,3,5-triaza -7-phosphaadamantane or its 7-oxide having the formula,

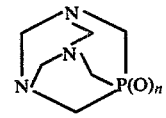

wherein n is an integer from 0 to 1, with three or more parts of a hydrohalic acid HX, where X is a halogen, until all three of the N—CH$_2$N bonds are cleaved, and recovering the product therefrom.

The main object of this invention is to prepare novel salts of tris(aminomethyl)phosphines and their oxides in which each and every amino group is in its ammonium salt form, i.e. each and every nitrogen atom bears a proton and a positive charge.

Another object of this invention is to prepare novel compounds that are useful as catalysts.

Other objects of the invention will be apparent from the following detailed description of the preferred embodiments of the invention.

DESCRIPTION OF THE PREFERRED EMBODIMENTS

The novel compounds of this invention have the formula $(R_2NH^+CH_2)_3P(O)_n 3X^-$ wherein R is hydrogen, an alkyl radical having from 1 to 6 carbon atoms or an aryl radical, n is an integer from 0 to 1, and X is a halogen.

In accordance with the practice of this invention, the new compounds may be prepared by any one of several methods.

One method consists of reacting a tris(aminomethyl)-phosphine or its oxide, having the structure $(R_2NCH_2)_3P(O)_n$ wherein R and n are as previously defined, with three or more parts of a hydrohalic acid, HX, until all three of the amino groups are converted into ammonium groups, and recovering the product therefrom.

Another method for preparing the new compounds of this invention consists of hydrolyzing a tris(N-carbalkoxylaminomethyl)phosphine oxide having the structure $(R'O_2CNHCH_2)_3PO$ wherein R' is an alkyl radical, with six or more parts of a hydrohalic acid, HX, until all three of the carbamate groups are cleaved, and recovering the product therefrom. The requiste tris(N-carbalkoxylaminomethyl)phosphine oxides may be prepared as described in our pending application, Ser. No. 964,852, filed 11/29/78, TRIS(N-CARBALKOXYLAMINOMETHYL)PHOSPHINE OXIDES & SULFIDES.

The success of this method is all the more remarkable when it is considered that carbamates having slightly different structures are cleaved in an entirely different manner. Carbamates having the following structures,

wherein R' and X are as defined above, suffer alkyl-nitrogen fission rather than acyl-nitrogen fission, giving phosphorus compounds having hydroxymethyl (HOCH$_2$) radicals rather than aminomethyl (NH$_2$CH$_2$) radicals. Such compounds are incapable of forming salts, and therefore do not fall within the scope of this invention.

Yet another method for preparing the new compounds of this invention consists of hydrolyzing 1,3,5-triaza-7-phosphaadamantane or its 7-oxide having the structure.

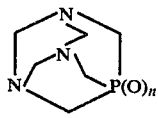

where n=0 to 1, with three or more parts of a hydrohalic acid, HX, until all three of the N—CH$_2$N bonds are cleaved, and recovering the product therefrom. The requiste 1,3,5-triaza-7-phosphaadamantane and its 7-oxide may be prepared as described by Daigle et al., J. Heterocyclic Chem. 11, 407 (1974).

We have further found that a product of this invention is obtained as a degradation product of the reaction of THCP with 1,1,3-trimethylurea. We believe that this degradation was the result of the use of a high reaction temperature in combination with a urea which, by virtue of its many alkyl substituents, was more basic than ureas having fewer alkyl substituents.

Tertiary phosphines are oxidizable substances. Some tertiary phosphines are so easily oxidized that they fume or inflame in air. This is particularly true of the lower tertiary alkyl phosphines, i.e. those containing alkyl residues having less than four carbon atoms. Such substances must be handled constantly in an inert atmosphere, such as nitrogen or argon, for any exposure to air is harmful.

It is therefore surprising, and not at all obvious even to those skilled in the art, to find that tris(aminomethyl)-phosphines, which, like other lower tertiary phosphines are easily oxidized and must be protected from the air, become air-stable and non-hygroscopic when transformed into the ternary tris(aminomethyl)phosphine salts of this invention.

We believe, without wishing to be bound by any specific hypothesis, that the reduced sensitivity to air and to moisture of the ternary salts of this invention are a consequence of the electron-withdrawing inductive effect exerted by the three ammonium groups on the phosphorus atom. This inductive effect tends to disperse the phosphorus lone pair electrons over the three adjacent bonds, making the phosphorus atom less susceptible to bonding with oxygen, water, and other electrophilic reagents. The effect can be illustrated as follows:

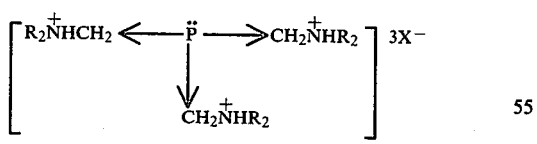

The same inductive effect is exerted by the three ammonium groups on the phosphoryl group (P=O or P→O ) in the ternary salts of tris(aminomethyl)phosphine oxide. The effect is manifested in their lack of hygroscopicity, and in the shift of the phosphoryl stretching frequency from 1140 cm$^{-1}$ to 1180 cm$^{-1}$ in their infrared spectra.

EXAMPLE 1

A rubber-capped serum bottle containing 25 ml of ethanol was purged of air with argon, and then charged by means of a syringe with 2.31 g (11.25 mmol) of tris(-dimethylaminomethyl)phosphine and 7.00 ml (42.0 mmol) of 6N hydrochloric acid. The solution, which fumed but remained clear, was shaken for 30 min and then stripped under vacuum, leaving 3.55 g (100% yield) of tris(dimethylaminomethyl)phosphine trihydrochloride as a white, crystalline solid.

A portion of this product was recrystallized from ethanol (50 ml/g), giving a pure sample, m.p. 209°–210° C. dec. The infrared spectrum of the product was identical to that of Example 5, with no evidence of P=O absorption in any fraction.

The product was soluble in water, methanol, hot ethanol and hot dimethylsulfoxide, and insoluble in chloroform, carbon tetrachloride, and other common organic solvents. In contrast to the free base, which fumed and oxidized spontaneously when exposed even momentarily to the air, the trihydrochloride was air-stable and non-hygroscopic.

EXAMPLE 2

Five ml (0.03mol) of a 6N hydrochloric acid solution was pipetted into a stoppered flask containing 2.21 g (0.01 mol) of tris(dimethyl aminomethyl)phosphine oxide. The mixture was shaken until the fuming and exotherming subsided, allowed to stand 30 min, and then stripped of water under vacuum, leaving 3.32 g (100% yield) of tris(dimethylaminomethyl)phosphine oxide trihydrochloride as a white, crystalline solid, m.p. 228°–229° C. dec.

A portion of this product was recrystallized from methanol (50 ml/g), giving an analytically pure sample, m.p. 234°–235° C. with reddening.

Anal.: Calcd. for C$_9$H$_{27}$Cl$_3$N$_3$OP; C, 32.69; H, 8.23; Cl, 32.16; N, 12.71; P, 9.37%. Found: C, 32.82; H, 8.46; CL, 32.15; N, 12.57; P, 9.49%.

The infrared spectrum of a portion of the product, mulled in Nujol, showed strong absorption peaks at 1180 (P=O) and 2400 to 2470 (NH+) cm$^{-1}$. The proton NMR spectrum of a portion of the product, dissolved in deuterium oxide, showed a singlet at δ 3.21 ppm assigned to the six methyl groups and a doublet at δ 4.31 ppm (J=7.0 Hz) assigned to the three methylene groups, and was free of impurity peaks. The uncharged phosphine oxide, in contrast, showed no NH peak in its infrared spectrum, and the methyl singlet and methylene doublet in its NMR spectrum were shifted to δ 2.42 ppm and 2.82 ppm (J=7.0 Hz), respectively.

The product was soluble in water, hot methanol, and hot dimethylsulfoxide, and insoluble in ethanol, acetic acid, or other common organic solvents. Unlike the uncharged phopshine oxide, the product was not hygroscopic.

EXAMPLE 3

This example and the example which follows illustrate the preparation of a product of this invention by the hydrolysis of a tris(N-carbalkoxylaminomethyl)-phosphine oxide with a mineral acid.

A solution of 31.12 g (0.1 mol) of tris(N-carbomethoxylaminomethyl)phosphine oxide in 100 ml of constant-boiling (47–49%) hydrobromic acid was heated to reflux with constant stirring. Within a few minutes, solids started to separate. The mixture was heated at reflux for one hour, cooled, and filtered. The filter cake, rinsed with ethanol and air-dried, afforded 18.95 g (49.9% yield) of tris(aminomethyl)phosphine oxide trihydrobromide as a white, crystalline solid, dec. 233° C. with reddening. Another 2.60 g (6.8% yield) was recovered from the filtrate after heating at reflux an additional hour.

A portion of this product was recrystallized twice from 90% ethanol (50 ml/g), giving an analytically pure sample, dec. 233° C. (reddening) without melting.

Anal.: Calcd. for $C_3H_{15}Br_3N_3OP$: C, 9.49; H, 3.98; Br, 63.10; N, 11.06; P, 8.16%. Found: C, 9.68; H, 4.02; Br, 62.90; N, 10.97; P, 8.26%.

The product gave a positive test for halogen (Beilstein test, blue-green flame), and a negative test for ammonia with 50% sodium hydroxide.

The infrared spectrum of a portion of the product, mulled in Nujol, showed very strong absorption peaks at 825 and 1180 (P=O) cm$^{-1}$, and strong peaks at 1540 to 1565 (NH+) and 2530 to 2600 (NH+) cm$^{-1}$. The proton NMR spectrum of a portion of the product, dissolved in deuterium oxide, showed only a methylene doublet at $\delta$ 4.10 ppm (J=7.5 Hz) assigned to the three methylene groups.

The tests, analyses and spectra each provided support for the assigned structure, and together they confirmed it.

The product was soluble in water and in hot dimethylsulfoxide, and insoluble in methanol, chloroform, and other common organic solvents. It was not hygroscopic, unlike the free base.

EXAMPLE 4

A solution of 9.34 g (0.03 mol) of tris(N-carbomethoxylaminomethyl)-phosphine oxide in 100 ml of constant-boiling (6N) hydrochloric acid was heated to reflux in an argon atomosphere and held at reflux until the gassing subsided (20 hr). No solids separated. The solution was cooled and then stripped of water and excess acid under vacuum, leaving 9.10 g of colorless oil.

The oil was taken up in 25 ml of water, transferred to a column packed with 50 g of Bio-Rad 50W-X4(a high porosity nuclear sulfonic acid cation exchange resin) and eluted, first with water to remove neutral substances (1.58 g), and then with 6N hydrochloric acid to remove ammonium salts (7.35 g ). The second salt fraction (0.58 g, 7.8% yield) was a white, crystalline solid identified as tris(aminomethyl)phosphine oxide trihydrochloride by comparison of its infrared spectrum with that of the product of Example 7.

EXAMPLE 5

A mixture of 9.53 g (0.05 mol) of tetrakis(hydroxymethyl)phosphonium chloride (THPC), 20.43 g (0.20 mol) of 1,1,3-trimethylurea and 75 ml of toluene was heated to reflux in an oil bath in an apparatus fitted with a Dean-Stark trap for azeotropic removal of water. Water began to separate when the bath temperature reached 136° C., and after 1 hr at 140° C. solids began to separate. Thirty minutes later, when the trap contained 3.5 ml of water (theor. 3.6 ml), the reaction mixture was cooled and filtered, giving 2.93 g (55.9% yield) of tris(-dimethylaminomethyl)phosphine trihydrochloride as a cream-colored solid, m.p. 192°-194° C. dec.

A portion of this product was recrystallized from ethanol (50 ml/g), giving an analytically pure sample, m.p. 209°-210° C. dec. No precautions were taken to exclude air, yet there was no evidence of oxidation.

Anal.: Calcd. for $C_9H_{27}Cl_3N_3P$: C, 34.35; H, 8.65; Cl, 33.80; N, 13.36%. Found: C, 33.77; H, 8.63; Cl, 33.20; N, 13.22%.

The infrared spectrum of a portion of the product, mulled in Nujol, showed strong absorption peaks at 965, 1005, 1120, 1270 and 2300 to 2600 (NH+) cm$^{-1}$. The proton NMR spectrum of a portion of the product, dissolved in deuterium oxide, showed a singlet at $\delta$ 3.10 ppm assigned to the six methyl groups, and a doublet at $\delta$ 3.95 ppm (J=1.5 Hz) assigned to the three methylene groups.

EXAMPLE 6

This example and the two examples which follow illustrate the preparation of a product of this invention by a hydrolysis of a 1,3,5-triaza-7-phosphaadamantane or its 7-oxide with a mineral acid.

A solution of 3.46 g (0.02 mol) of 1,3,5-triaza-7-phosphaadamantane-7-oxide, 25 g (0.15 mol) of 48% hydrobromic acid and 40 g of water was poured onto a watch glass and allowed to evaporate at room temperature. After three days, the product was collected on a filter and washed twice with 100 ml volumes of hot methanol, giving 5.6 g (73% yield) of a white crystalline solid identified as tris(amino methyl)phosphine oxide trihydrobromide by comparison of its infrared spectrum with that of the product of Example 3.

EXAMPLE 7

Following the procedure outline in Example 6, the 1,3,5-triaza-7-phosphaadamantane-7-oxide (7.92 g, 0.04 mol) was hydrolyzed with a solution of 22 g (0.22 mol) of 37.7% hydrochloric acid and 80 g of water, giving, after workup, 5.9 g (60% yield) of tris(aminomethyl)-phosphine oxide trihydrochloride, dec. 239° C. without melting.

Anal.: Calcd. for $C_3H_{15}Cl_3N_3OP$: C, 14.60; H, 6.13; Cl, 43.14; N, 17.04; P, 12.56, Found: C, 14.59; H, 6.11; Cl, 43.29; N, 17.46; P, 12.45.

The infrared spectrum of a portion of the product, pressed in a disk of potassium bromide, showed very strong absorption peaks at 820 and 1180 (P=O) cm$^{-1}$,and a strong peak at 1550 (NH+) cm$^{-1}$. The proton NMR spectrum of a portion of the product, dissolved in deuterium oxide, showed only a methylene doublet at $\delta$ 3.95 ppm (J=7.5 Hz).

EXAMPLE 8

Following the procedure outline in Example 6, 3.14 g (0.02 mol) of 1,3,5-triaza-7-phosphaadamantane was hydrolyzed with a solution of 25 g (0.15 mol) of 48% hydrobromic acid and 40 g of water, giving, after workup, 5.4 g (74% yield) of tris(aminomethyl)phosphine trihydrobromide as a white, crystalline solid, dec. 214° C. without melting.

Anal.: Calcd. for $C_3H_{15}Br_3N_3P$: C, 9.89; H, 4.18; Br, 65.87; N, 11.54; P, 8.51. Found: C, 10.00; H, 4.24; Br, 65.51; N, 11.37; P, 8.62.

The infrared spectrum of a portion of the product, pressed in a disk of potassium bromide, showed a strong absorption peak at 1550 (NH+) cm $^{-1}$. The proton NMR spectrum of a portion of the product, dissolved in deuterium oxide, showed only a methylene singlet at $\delta$ 3.63 ppm.

The novel ternary salts of this invention were found to be useful as catalysts for the chemical reactions employed in the finishing of cotton textiles with methylol amide crosslinking agents. These agents are used extensively in the textile industry to impart wrinkle resistance and durable press properties to cotton and cotton blend fabrics. In fact, the majority of textile materials, both wearing apparel and household articles, offered in the marketplace exhibit these properties to some useful degree. Many synthetic fibers possess inherent resiliency and wrinkle resistance, but cellulose-based fibers such as cotton need to be chemically treated to aquire these properties.

The principal chemical treatments employed in the finishing of cotton textile fabrics are those in which the cellulose is crosslinked, generally by reaction with a di- or multi-functional reagent. Most of the crosslinking agents employed in the finishing industry are of the methylol amide type, and these generally require an acid or latent acid catalyst for maximum effectiveness. The state of the art relating to catalysts used for producing wrinkle resistant cellulose-based textiles is discussed by Marsh in "Self-Smoothing Fabrics," Chapman and Hall, Ltd. London, 1962, pp. 112–132, and by Mark, Wooding and Atlas in "Chemical After-treatment of Textiles," Wiley-Interscience, New York, 1971, pp. 417–464.

The following examples are given to illustrate the use of the novel ternary salts of this invention as catalysts for applying one such crosslinking agent, dimethylol dihydroxyethyleneurea (hereafter referred to as DMDHEU) to cotton printcloth. They are given merely as illustrations, and should not be considered as limiting the scope of the invention. The durable press (DP) ratings were determined by standard test methods, using AATCC Test Method 124–1968, Procedure IIIB, of the AmericanAssociation of Textile Chemists and Colorists.

EXAMPLE 9

A 12"×24" swatch of 80 ×80 desized, scoured and bleached cotton printcloth was immersed in a solution of 9 g of DMDHEU, 0.5 g of tris(aminomethyl)phosphine oxide trihydrochloride and 90.5 g of water, padded to about a 90% wet pickup, mounted on a pin frame, dried at 60° C. for 7 min. in an oven with mechanically circulating air, cured at 160° C. for 3 min. in a similar oven, removed from the pin frame, and then machine washed and tumble dried. The durable press (DP) rating of the finished fabric is compared in Table I with that of an untreated control that was also machine washed and tumble dried.

Table I

| Catalyst | DP Rating |
| --- | --- |
| $(NH_2CH_2)_3PO.3HCl$ | 4.0 |
| None (untreated) | 1.0 |

A DP rating of 3.0 is considered adequate for imparting wrinkle resistance and a smooth drying appearance to a cotton fabric; a rating of 4.0 is considered superior. This example demonstrates that tris(aminomethyl)phosphine oxide trihydrochloride is an effective catalyst for applying DMDHEU to cotton.

EXAMPLES 10 to 12

Three 12"×24" swatches of cotton printcloth were treated with DMDHEU as described in Example 9, except that the quantity of catalyst was varied from 0.5 g to 2.0 g. Results are shown in Table II.

Table II

| Example | Catalyst, g | DP Rating | Color |
| --- | --- | --- | --- |
| 10 | 0.5 | 4.0 | White |
| 11 | 1.0 | 4.0 | Yellow |

Table II-continued

| Example | Catalyst, g | DP Rating | Color |
| --- | --- | --- | --- |
| 12 | 2.0 | 3.5 | Brown |

It is seen that the DP rating is good at any catalyst concentration, but the fabric becomes discolored as the catalyst concentration increases. This behavior is not uncommon for strongly acidic catalysts.

EXAMPLES 13 to 15

Three 12"×24" swatches of cotton printcloth were treated with DMDHEU as described in Examples 10 to 12, but omitting the 3 min cure at 160° C. Results are shown in Table III Table III

| Example | Catalyst, g | DP Rating | Color |
| --- | --- | --- | --- |
| 13 | 0.5 | 2.4 | White |
| 14 | 1.0 | 3.3 | White |
| 15 | 2.0 | 3.0 | White |

It is seen that the catalyst is effective even at temperatures as low as 60° C. (the drying temperature), is increased. To those skilled in the art, only the DP rating of Example 13 will be unacceptable, although still significantly higher than the control.

EXAMPLES 16 to 20

Five 12"×24" swatches of cotton printcloth were treated with DMDHEU as described in Example 9, except that the curing temperature was varied from 100° C. to 140° C. Results are shown in Table IV.

Table IV

| Example | Cure Temp. °C. | DP Rating |
| --- | --- | --- |
| 16 | 100 | 3.7 |
| 17 | 110 | 4.0 |
| 18 | 120 | 4.0 |
| 19 | 130 | 4.3 |
| 20 | 140 | 3.9 |

It is seen that the catalyst is effective over the entire range of temperatures from 100° C. (Example 16) to 160° C. (Example 9).

EXAMPLES 21 to 25

Five 12"×24" swatches of cotton printcloth were treated with DMDHEU as described in Examples 16 to 20, except that the catalyst was changed to tris-(aminomethyl)phosphine trihydrobromide, $(NH_2CH_2)_3P.3HBr$. The quantity of catalyst and other treating conditions were unchanged. Results are shown in Table V.

Table V

| Example | Cure Temp. °C. | DP Rating |
| --- | --- | --- |
| 21 | 100 | 3.5 |
| 22 | 110 | 4.0 |
| 23 | 120 | 3.9 |
| 24 | 130 | 4.3 |
| 25 | 140 | 4.2 |

It is seen that this catalyst is as effective as the catalyst of Examples 16 to 20 over the same range of curing temperatures.

The foregoing examples are given for clearness of understanding only, and are not intended to limit the scope of the invention in any way, as modifications will be obvious to those skilled in the art.

We claim:

1. Ternary salts of tris (aminomethyl)phosphine and its oxide having the formula;

$$(R_2NH^+CH_2)_3P(O)_n 3X^-$$

wherein R is a radical selected from the group consisting of hydrogen, alkyl having from 1 to 6 carbon atoms, and aryl, n is an integer from 0 to 1, and X is a halogen.

2. The compound of claim 1 wherein n is 0 and X is chlorine.

3. The compound of claim 1 wherein n is 0 and X is bromine.

4. The compound of claim 1 wherein n is 1 and X is bromine.

5. The compound of claim 1 wherein n is 1 and X is chlorine.

* * * * *